United States Patent [19]
Kim et al.

[11] Patent Number: 5,919,400
[45] Date of Patent: Jul. 6, 1999

[54] STABILIZED ISOTHIAZOLONE SOLUTION

[75] Inventors: Seung Hwan Kim, Suwon; Jin Soo Lim, Gwacheon; Jin Man Kim; Myung Ho Cho, both of Suwon, all of Rep. of Korea

[73] Assignee: Sunkyong Industries Co., Ltd., Kyungki-do, Rep. of Korea

[21] Appl. No.: 08/942,791

[22] Filed: Oct. 2, 1997

[30] Foreign Application Priority Data

Dec. 5, 1996 [KR] Rep. of Korea .................. 96-61926

[51] Int. Cl.⁶ .................. A01N 43/80; A61K 31/425; C07D 275/03; C09K 15/30
[52] U.S. Cl. .................. 252/405; 252/406; 252/407; 514/372; 548/213
[58] Field of Search ............... 548/213; 514/372; 252/405, 407, 406

[56] References Cited

U.S. PATENT DOCUMENTS

| | | | |
|---|---|---|---|
| 3,870,795 | 3/1975 | Miller et al. | 424/270 |
| 4,067,878 | 1/1978 | Miller et al. | 260/302 A |
| 4,939,266 | 7/1990 | Bayer et al. | 548/213 |
| 5,210,094 | 5/1993 | Reeve | 514/372 |
| 5,725,806 | 3/1998 | Ghosh | 252/405 |

*Primary Examiner*—Johann Richter
*Assistant Examiner*—Jane Oswecki
*Attorney, Agent, or Firm*—Finnegan, Henderson, Farabow, Garrett & Dunner, L.L.P.

[57] ABSTRACT

This invention relates to a stabilized isothiazolone solution and more particularly, to a stabilized isothiazolone solution comprising isothiazolone expressed by the following formula (I), stabilizer expressed by the following formula (II), and organic solvent diffusing these compounds effectively:

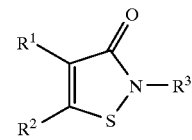

(I)

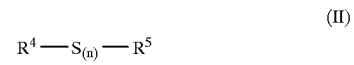

(II)

In these formulae, n, $R^1$, $R^2$, $R^3$, $R^4$, and $R^5$ have the same definitions as defined in the detailed description of this application, respectively.

8 Claims, No Drawings

000
STABILIZED ISOTHIAZOLONE SOLUTION

BACKGROUND OF THE INVENTION

1. Field of the Invention

This invention relates to a stabilized isothiazolone solution and more particularly, to a stabilized isothiazolone solution comprising isothiazolone expressed by the following formula (I), stabilizer expressed by the following formula (II), and organic solvent diffusing these compounds effectively.

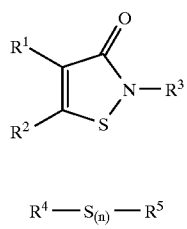

$$R^4 - S_{(n)} - R^5 \quad (II)$$

In these formulae:

n is 1 or 2;

$R^1$ and $R^2$ are the same or different, respectively, representing a hydrogen atom; a halogen atom; or a $C_1$~$C_4$ alkyl group;

$R^3$ represents a hydrogen atom; a $C_1$~$C_{10}$ alkyl group which is substituted or unsubstituted with a halogen atom or a hydroxy group; a $C_2$~$C_{10}$ alkenyl group which is substituted or unsubstituted with a halogen atom; a $C_2$~$C_{10}$ alkynyl group which is substituted or unsubstituted with a halogen atom; or an aralkyl group which is substituted or unsubstituted with a halogen atom, a $C_1$~$C_{10}$ alkyl group, or a $C_2$~$C_9$ alkoxy group;

$R^4$ and $R^5$ are the same or different, respectively, representing a hydrogen atom; a halogen atom; a $C_1$~$C_{10}$ alkyl group which is substituted or unsubstituted with a halogen atom or a hydroxy group; a $C_2$~$C_{10}$ alkenyl group which is substituted or unsubstituted with a halogen atom; a $C_2$~$C_{10}$ alkynyl group which is substituted or unsubstituted with a halogen atom; an aralkyl group which is substituted or unsubstituted with a halogen atom a $C_1$~$C_{10}$ alkyl group, or a $C_2$~$C_9$ alkoxy group; or a group expressed by the following formula (III-1) or (III-2):

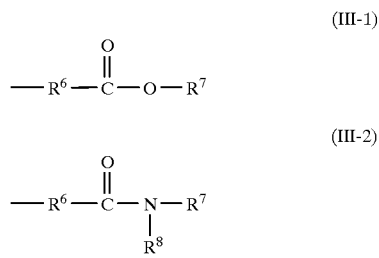

wherein:

$R^6$ is a halogen atom or a $C_1$~$C_{10}$ alkyl group which is substituted or unsubstituted with a halogen atom or a hydroxy group; a $C_2$~$C_{10}$ alkenyl group which is substituted or unsubstituted with a halogen atom; a $C_2$~$C_{10}$ alkynyl group which is substituted or unsubstituted with a halogen atom; an aralkyl group which is substituted or unsubstituted with a halogen atom, a $C_1$~$C_{10}$ alkyl group, or a $C_2$~$C_9$ alkoxy group; $R^7$ and $R^8$ are the same or different, respectively, representing a hydrogen atom; a halogen atom; a $C_1$~$C_{10}$ alkyl group which is substituted or unsubstituted with a halogen atom or a hydroxy group; a $C_2$~$C_{10}$ alkenyl group which is substituted or unsubstituted with a halogen atom; a $C_2$~$C_{10}$ alkynyl group which is substituted or unsubstituted with a halogen atom; an aralkyl group which is substituted or unsubstituted with a halogen atom, a $C_1$~$C_{10}$ alkyl group, or a $C_2$~$C_9$ alkoxy group.

2. Description of the Related Art

Since its development by Craw et al. in 1965, isothiazolone compound has been extensively used in the industrial field as a disinfectant, including an antibacterial and antimicrobial agent for dyes, cosmetics, fibers, or plastics, etc.

However, since the extremely unstable isothiazolone compound is easily degraded by moisture in the air and ultraviolet light, the beneficial properties of the final product may be lost during storage. In order to improve the stability of isothiazolone compound, several methods have been under active development, and among them, the typical method is to use a metal salt stabilizer.

In U.S. Pat. Nos. 3,870,795 and 4,067,878, for example, the stabilization of isothiazolone compound has been approached by reducing chemical degradation with the addition of metal nitrite or metal nitrate, but such metal salt stabilizers are reacted with emulsion components in a latex emulsion solution diffused with polymers, thus developing agglutination or precipitates. Further, in any reaction system, corrosion in the system may occur due to chlorine ions combined with metal salt. Thus, the removal of metal salt in such a system is a prerequisite.

SUMMARY OF THE INVENTION

The inventors have endeavored to cope with the aforementioned disadvantages associated with conventional methods for stabilizing isothiazolone. With the notion that the degradation of isothiazolone may be prevented in such a manner by adding a sulfur-containing compound expressed by formula (II) to the composition containing the isothiazolone compound, the inventors have completed this invention.

The object of this invention is to provide a stabilized isothiazolone solution which is effective as an antimicrobial agent.

DETAILED DESCRIPTION OF THE INVENTION

This invention relates to stabilized isothiazolone solution where stabilizers and solvents are blended with isothiazolone, and more particularly, to stabilized isothiazolone solutions comprising isothiazolone expressed by the formula (I), a stabilizer expressed by the following formula (II), and organic solvent:

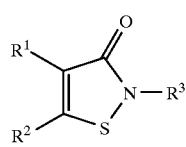

-continued

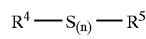
(II)

wherein:

n, $R^1$, $R^2$, $R^3$, $R^4$, and $R^5$ have the same definitions as defined above, respectively.

Further, this invention includes a method of stabilizing isothiazolone by blending isothiazolone expressed by formula (I) with an effective amount of stabilizer expressed by formula (II).

In addition, this invention includes a method of inhibiting the growth of microorganisms by applying an effective amount of isothiazolone solution, so stabilized, to the contaminated or contamination-vulnerable range by microorganisms or over the range.

This invention is described in more detail as set forth hereunder.

This invention relates to isothiazolone solution wherein a sulfur containing compound expressed by formula (II), a stabilizer, is blended with the isothiazolone compound which is unstable in the air, so as to stabilize the isothiazolone compound.

The isothiazolone compound which may be used in this invention, includes one or more compounds selected from the group expressed by formula (I), preferably one or more compounds selected from the group containing 5-chloro-2-methyl-4-isothiazolin-3-one, 2-methyl-4-isothiazolin-3-one, 2-n-octyl-4-isothiazolin-3-one, 4,5-dichloro-2-cyclohexyl-4-isothiazolin-3-one and 4,5-dichloro-2-n-octyl-4-isothiazolin-3-one. It is more preferably to use a single 5-chloro-2-methyl-4-isothiazolin-3-one or a mixture of 5-chloro-2-methyl-4-isothiazolin-3-one and 2-methyl-4-isothiazolin-3-one. When producing a mixture of 5-chloro-2-methyl-4-isothiazolin-3-one and 2-methyl-4-isothiazolin-3-one, its blending ratio is preferably about 60:40~99:1 wt %, more preferably about 65:35~95:5 wt %.

In one embodiment, it is preferable to provide a compound containing 2-methyl-4-isothiazolin-3-one as an active ingredient where a small amount of 5-chloro-2-methyl-4-isothiazolin-3-one is blended. In such case, the preferable blending ratio is about 98:2~96:4 wt %, and a particularly preferable blending ratio is about 97:3 wt %.

The stabilizer used in the manufacture of stabilized isothiazolone solution according to this invention is one or more compounds selected from sulfur-containing compounds expressed by formula (II). It is preferable to use one or more compounds selected from the following group: N,N'-dimethyl-3,3'-dithiodipropionamide, N,N'-dimethyl-3-thiodipropionamide, methyl-3-mercaptopropionamide, 3,3-dithiodimethyl dipropionate, 3-thiodimethyl dipropionate and methyldisulfide.

According to this invention, any type of organic solvent to effectively diffuse the isothiazolone compound and stabilizer may be used.

The stabilized isothiazolone of this invention may be manufactured in the form of a solution. Depending on its use, concentrated or diluted solutions may be manufactured, and when stabilized isothiazolone is employed in exceptional cases such as mass shipments, more concentrated solutions may be used. Its blending ratio comprises about 0.00001~99 wt % of one or more compounds selected from isothiazolone expressed by formula (I), 0.00001~99 wt % of stabilizer expressed by formula (II), and less than 99.99998 wt % of organic solvent. The preferable blending ratio comprises 0.1~20 wt % of one or more compounds selected from isothiazolone expressed by formula (I), 0.1~10 wt % of stabilizer expressed by formula (II), and 70~99.8 wt % of organic solvent. The most preferable blending ratio comprises 1~15 wt % of one or more compounds selected from isothiazolone expressed by formula (I), 1~5 wt % of stabilizer expressed by formula (II), and 80~98 wt % of organic solvent.

According to this invention, the amount of stabilizer may vary under blending conditions and isothiazolone concentration with a mixture; stabilizer is preferably blended with isothiazolone in the ratio of 1:0.01~1,000 weight in terms of stability and cost-saving. In the case of a concentrated solution, stabilizer is preferably blended with isothiazolone in the ratio of 1:0.02~1:50 weight, and even though this level may be exceeded, this is uneconomical. In the case of an extremely diluted isothiazolone solution (isothiazolone of about 1~10,000 ppm within solvent), stabilizer is preferably blended with isothiazolone in the ratio of 1:0.1~1:20 weight, more preferably in the ratio of 1:0.2~1:20 weight.

The stabilized isothiazolone solution according to this invention comprises sulfur-containing compound expressed by formula (II) so as to stabilize the isothiazolone compound. Thus, the amount of sulfide treated in the system is quite small, and it does not prevent other substances required for protection in the system or protection-applied system.

As aforementioned, the stabilized isothiazolone solution according to this invention is very stable in the air, and its efficacy may be sustained under a relatively prolonged period of time in storage. Further, the stabilized isothiazolone solution according to this invention exhibits excellent antimicrobial activities when its effective amount is applied to the contaminated or contamination-vulnerable range by bacteria, microorganisms or algae, or over the range.

In other words, the stabilized isothiazolone solution may be extensively employed in the following fields: germicidal agents, sanitary aids, purifier, deodorizer, soap in the form of liquid or powder, anti-oil and anti-greasing agents, chemical products for the treatment of foods, daily chemical products, food protectives, protectives for animal feeds, wood protectives, dyes, lazures, flavoring agents, medical preservatives including hospital, metal agents, dyeing solutions, cooling water, air purifier, petroleum manufacture, paper-treatment, anti-slime agent at a paper mill, petroleum products, adhesives, fibers, paint slurry, latex, treatment for leather articles, petroleum fuels, laundry disinfectants, blending feeds for farming, ink, mining, non-woven fabric, petroleum reservoirs, paste material, rubber, sugar refining, tobacco, swimming pool, cosmetics, commodities for toilet, pastes, plastics, cardboard, pharmaceuticals, chemical toilet paper, household laundries, additives for diesel fuel, wax, cork, lubricants, commodities for construction, blending or polishing agents for concrete; it also may be used in the atmosphere where organic materials come in contact with other undesirable microorganisms, or places where such microorganisms may be grown, or in any places having water.

This invention is explained in more detail by the following examples, but the claims are not limited to these examples.

All percentages are wt %, and in the case of all reagents used in this invention, they are industrial reagents in proper state.

Further, each isothiazolone solution, so obtained from the following examples and comparative examples, is left in a thermostat at 65° C. to measure their thermal stabilities. The degradation status induced by thermal stability measurement was measured by high performance liquid chromatography (HPLC).

According to this invention, the thermal stability was measured at 65° C., but in general, the same thermal stability effects are maintained as shown below:

The thermal stability measured during one week at 65° C. corresponds to that during 7 months at 25° C.;

The thermal stability measured during two weeks at 65° C. corresponds to that during 14 months at 25° C.;

The thermal stability measured during three weeks at 65° C. corresponds to that during 21 months at 25° C.;

The thermal stability measured during four weeks at 65° C. corresponds to that during 28 months at 25° C.

EXAMPLE 1

Isothiazolone solution was prepared by blending 14 wt % of an isothiazolone mixture comprising 5-chloro-2-methyl-4-isothiazolin-3-one and 2-methyl-4-isothiazolin-3-one in a weight ratio of 3:1, 3 wt % of 3,3-dithiodimethyl-dipropionate, and 83 wt % of organic solvent, as shown in the following table 1. The results of residual contents are represented in the following table 1.

TABLE 1

(unit: %)

| Classification | Beginning | Term (day) | | | | | | | | |
|---|---|---|---|---|---|---|---|---|---|---|
| | | 1st | 3rd | 5th | 7th | 10th | 14th | 17th | 20th | 24th |
| Ethylene glycol | 100 | 100 | 100 | 100 | 100 | 100 | 100 | 100 | 99 | 14 |
| Diethylene glycol | 100 | 100 | 100 | 100 | 100 | 100 | 100 | 100 | 98 | 5 |
| Ethylene glycol monomethyl ether | 100 | 100 | 100 | 100 | 100 | 100 | 90 | 5 | 0 | 0 |
| Ethylene glycol dimethyl ether | 100 | 100 | 100 | 100 | 100 | 100 | 100 | 90 | 5 | 0 |

EXAMPLE 2

Isothiazolone solution was prepared by blending 14 wt % of an isothiazolone mixture comprising 5-chloro-2-methyl-4-isothiazolin-3-one and 2-methyl-4-isothiazolin-3-one in a weight ratio of 3:1, 3 wt % of 3-thiodimethyldipropionate, and 83 wt % of organic solvent, as shown in the following table 2. The results of residual contents are represented in the following table 2.

TABLE 2

(unit: %)

| Classification | Beginning | Term (day) | | | | | | | |
|---|---|---|---|---|---|---|---|---|---|
| | | 1st | 3rd | 5th | 7th | 10th | 14th | 17th | 20th |
| Ethylene glycol | 100 | 100 | 100 | 100 | 100 | 100 | 100 | 95 | 20 |
| Diethylene glycol | 100 | 100 | 100 | 100 | 100 | 100 | 100 | 92 | 0 |
| Ethylene glycol monomethyl ether | 100 | 100 | 100 | 100 | 100 | 100 | 100 | 89 | 0 |
| Ethylene glycol dimethyl ether | 100 | 100 | 100 | 100 | 100 | 100 | 90 | 0 | 0 |

EXAMPLE 3

Isothiazolone solution was prepared by blending 14 wt % of an isothiazolone mixture comprising 5-chloro-2-methyl-4-isothiazolin-3-one and 2-methyl-4-isothiazolin-3-one in a weight ratio of 3:1, 3 wt % of methyldisulfide, and 83 wt % of organic solvent, as shown in the following table 3. The results of residual contents are represented in the following table 3.

TABLE 3

(unit: %)

| Classification | Beginning | Term (day) | | | | | | | |
|---|---|---|---|---|---|---|---|---|---|
| | | 1st | 3rd | 5th | 7th | 10th | 14th | 17th | 20th |
| Ethylene glycol | 100 | 100 | 100 | 100 | 100 | 100 | 95 | 0 | 0 |
| Diethylene glycol | 100 | 100 | 100 | 100 | 100 | 100 | 100 | 80 | 0 |

TABLE 3-continued

| | | | | Term (day) | | | | | (unit: %) |
|---|---|---|---|---|---|---|---|---|---|
| Classification | Beginning | 1st | 3rd | 5th | 7th | 10th | 14th | 17th | 20th |
| Ethylene glycol monomethyl ether | 100 | 100 | 100 | 100 | 100 | 99 | 95 | 15 | 0 |
| Ethylene glycol dimethyl ether | 100 | 100 | 100 | 100 | 100 | 95 | 13 | 0 | 0 |

EXAMPLE 4

Isothiazolone solution was prepared by blending 14 wt % of an isothiazolone mixture comprising 5-chloro-2-methyl-4-isothiazolin-3-one and 2-methyl-4-isothiazolin-3-one in a weight ratio of 3:1, 1 wt % of 3,3-dithiodimethyldipropionate, 1 wt % 3-thiodimethyldipropionate (stabilizer), 1 wt % methyldisulfide (stabilizer), and 83 wt % of organic solvent, as shown in the following table 4. The results of residual contents are represented in the following table 4.

TABLE 4

| | | | | | Term (day) | | | | | (unit: %) |
|---|---|---|---|---|---|---|---|---|---|---|
| Classification | Beginning | 1st | 3rd | 5th | 7th | 10th | 14th | 17th | 20th | 24th |
| Ethylene glycol | 100 | 100 | 100 | 100 | 100 | 100 | 100 | 100 | 95 | 5 |
| Diethylene glycol | 100 | 100 | 100 | 100 | 100 | 100 | 100 | 100 | 100 | 100 |
| Ethylene glycol monomethyl ether | 100 | 100 | 100 | 100 | 100 | 100 | 100 | 100 | 95 | 3 |
| Ethylene glycol dimethyl ether | 100 | 100 | 100 | 100 | 100 | 100 | 85 | 2 | 0 | 0 |

EXAMPLE 5

Isothiazolone solution was prepared by blending 14 wt % of an isothiazolone mixture comprising 5-chloro-2-methyl-4-isothiazolin-3-one and 2-methyl-4-isothiazolin-3-one in a weight ratio of 3:1, 3 wt % of N,N'-dimethyl-3,3'-dithiodipropionamide, and 83 wt % of organic solvent, as shown in the following table 5. The results of residual contents are represented in the following table 5.

TABLE 5

| | | | | Term (day) | | | | | (unit: %) |
|---|---|---|---|---|---|---|---|---|---|
| Classification | Beginning | 1st | 3rd | 5th | 7th | 10th | 14th | 17th | 20th |
| Ethylene glycol | 100 | 100 | 100 | 100 | 100 | 100 | 100 | 95 | 15 |
| Diethylene glycol | 100 | 100 | 100 | 100 | 100 | 100 | 100 | 95 | 80 |
| Ethylene glycol monomethyl ether | 100 | 100 | 100 | 100 | 100 | 99 | 99 | 98 | 95 |
| Ethylene glycol dimethyl ether | 100 | 100 | 100 | 100 | 100 | 99 | 99 | 98 | 95 |

EXAMPLE 6

Isothiazolone composition was prepared by blending 14 wt % of an isothiazolone mixture comprising 5-chloro-2-methyl-4-isothiazolin-3-one and 2-methyl-4-isothiazolin-3-one in a weight ratio of 3:1, 3 wt % of N,N'-dimethyl-3-thiodipropionamide, and 83 wt % of organic solvent, as shown in the following table 6. The results of residual contents are represented in the following table 6.

TABLE 6

(unit: %)

| Classification | Beginning | 1st | 3rd | 5th | 7th | 10th | 14th | 17th | 20th |
|---|---|---|---|---|---|---|---|---|---|
| Ethylene glycol | 100 | 100 | 100 | 100 | 100 | 100 | 100 | 100 | 95 |
| Diethylene glycol | 100 | 100 | 100 | 100 | 100 | 100 | 100 | 100 | 100 |
| Ethylene glycol monomethyl ether | 100 | 100 | 100 | 100 | 100 | 100 | 100 | 100 | 90 |
| Ethylene glycol dimethyl ether | 100 | 100 | 100 | 100 | 100 | 100 | 100 | 95 | 0 |

EXAMPLE 7

Isothiazolone composition was prepared by blending 14 wt % of an isothiazolone mixture comprising 5-chloro-2-methyl-4-isothiazolin-3-one and 2-methyl-4-isothiazolin-3-one in a weight ratio of 3:1, 3 wt % of methyl-3-mercaptopropionamide, and 83 wt % of organic solvent, as shown in the following table 7. The results of residual contents are represented in the following table 7.

TABLE 7

(unit: %)

| Classification | Beginning | 1st | 3rd | 5th | 7th | 10th | 14th | 17th | 20th |
|---|---|---|---|---|---|---|---|---|---|
| Ethylene glycol | 100 | 100 | 100 | 100 | 100 | 99 | 85 | 0 | 0 |
| Diethylene glycol | 100 | 100 | 100 | 100 | 100 | 100 | 99 | 50 | 10 |
| Ethylene glycol monomethyl ether | 100 | 100 | 100 | 100 | 100 | 99 | 80 | 17 | 0 |
| Ethylene glycol dimethyl ether | 100 | 100 | 100 | 100 | 100 | 99 | 50 | 0 | 0 |

EXAMPLE 8

Isothiazolone composition was prepared by blending 14 wt % of an isothiazolone mixture comprising 5-chloro-2-methyl-4-isothiazolin-3-one and 2-methyl-4-isothiazolin-3-one in a weight ratio of 3:1, 1 wt % of N,N'-dimethyl-3,3'-dithiodipropionamide, 1 wt % of N,N'-dimethyl-3-thiodipropionamide, 1 wt % of methyl-3-mercapto propionamide, and 83 wt % of organic solvent, as shown in the following table 8. The results of residual contents are represented in the following Table 8.

TABLE 8

(unit: %)

| Classification | Beginning | 1st | 3rd | 5th | 7th | 10th | 14th | 17th | 20th |
|---|---|---|---|---|---|---|---|---|---|
| Ethylene glycol | 100 | 100 | 100 | 100 | 100 | 100 | 100 | 95 | 50 |
| Diethylene glycol | 100 | 100 | 100 | 100 | 100 | 100 | 95 | 70 | 2 |
| Ethylene glycol monomethyl ether | 100 | 100 | 100 | 100 | 100 | 99 | 85 | 70 | 3 |
| Ethylene glycol dimethyl ether | 100 | 100 | 100 | 100 | 100 | 100 | 100 | 98 | 15 |

Comparative Example

Isothiazolone composition was prepared by blending 14 wt % of an isothiazolone mixture comprising 5-chloro-2-methyl-4-isothiazolin-3-one and 2-methyl-4-isothiazolin-3-one in a weight ratio of 3:1 and 86 wt % of organic solvent, as shown in the following table 9. The results of residual contents are represented in the following table 9.

TABLE 9

| | | | | Term (day) | | | | | (unit: %) |
|---|---|---|---|---|---|---|---|---|---|
| Classification | Beginning | 1st | 3rd | 5th | 7th | 10th | 14th | 17th | 20th |
| Ethylene glycol | 100 | 100 | 100 | 100 | 12 | 5 | 0 | 0 | 0 |
| Diethylene glycol | 100 | 100 | 100 | 100 | 100 | 95 | 0 | 0 | 0 |
| Ethylene glycol monomethyl ether | 100 | 100 | 100 | 99 | 40 | 0 | 0 | 0 | 0 |
| Ethylene glycol dimethyl ether | 100 | 100 | 100 | 99 | 15 | 0 | 0 | 0 | 0 |

While the invention has been described in terms of various preferred embodiments and specific examples, those skilled in the art will recognize that various changes and modifications can be made without departing from the spirit and scope of the invention, as defined in the appended claims.

This application claims priority benefits under 35 U.S.C. § 119 based on Republic of Korea Patent Application No. 96-61926, filed Dec. 5, 1996. This Korean application is entirely incorporated herein by reference.

What is claimed is:

1. A stabilized isothiazolone solution comprising an isothiazolone or isothiazolones blended with stabilizer and solvent and which comprises isothiazolone expressed by the following formula (I), a non-aromatic stabilizer expressed by the following formula (II), and organic solvent:

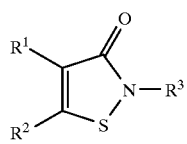
(I)

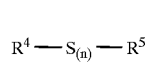
(II)

wherein:

n is 1 or 2;

$R^1$ and $R^2$ are the same or different, respectively, representing a hydrogen atom; a halogen atom; or a $C_1$~$C_4$ alkyl group;

$R^3$ represents a hydrogen atom; a $C_1$~$C_{10}$ alkyl group which is substituted or unsubstituted with a halogen atom or a hydroxy group; a $C_2$~$C_{10}$ alkenyl group which is substituted or unsubstituted with a halogen atom; a $C_2$~$C_{10}$ alkynyl group which is substituted or unsubstituted with a halogen atom; or an aralkyl group which is substituted or unsubstituted with a halogen atom, a $C_1$~$C_{10}$ alkyl group, or a $C_2$~$C_9$ alkoxy group;

$R^4$ and $R^5$ are non-aromatic are the same or different, respectively, representing a hydrogen atom; a $C_1$~$C_{10}$ alkyl group which is substituted or unsubstituted with a halogen atom or a hydroxy group; a $C_2$~$C_{10}$ alkenyl group which is substituted or unsubstituted with a halogen atom; a $C_2$~$C_{10}$ alkynyl group which is substituted or unsubstituted with a halogen atom; an aralkyl group which is substituted or unsubstituted with a halogen atom, a $C_1$~$C_{10}$ alkyl group, or a $C_2$~$C_9$ alkoxy group; or a group expressed by the following formula (III-1) or (III-2):

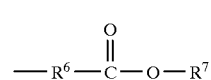
(III-1)

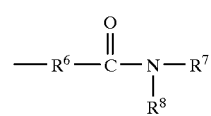
(III-2)

wherein:

$R^6$ is a $C_1$~$C_{10}$ alkyl group which is substituted or unsubstituted with a halogen atom or a hydroxy group; a $C_2$~$C_{10}$ alkenyl group which is substituted or unsubstituted with a halogen atom; a $C_2$~$C_{10}$ alkynyl group which is substituted or unsubstituted with a halogen atom; an aralkyl group which is substituted or unsubstituted with a halogen atom, a $C_1$~$C_{10}$ alkyl group, or a $C_2$~$C_9$ alkoxy group; $R^7$ and $R^8$ are the same or different, respectively, representing a hydrogen atom; a $C_1$~$C_{10}$ alkyl group which is substituted or unsubstituted with a halogen atom or a hydroxy group; a $C_2$~$C_{10}$ alkenyl group which is substituted or unsubstituted with a halogen atom; a $C_2$~$C_{10}$ alkynyl group which is substituted or unsubstituted with a halogen atom; an aralkyl group which is substituted or unsubstituted with a halogen atom, a $C_1$~$C_{10}$ alkyl group, or a $C_2$~$C_9$ alkoxy group.

2. The stabilized isothiazolone solution according to claim 1, wherein said solution comprises an isothiazolone or isothiazolones selected from the group consisting of 5-chloro-2-methyl-4-isothiazolin-3-one, 2-methyl-4-isothiazolin-3-one, 2-n-octyl-4-isothiazolin-3-one, 4,5-dichloro-2-cyclohexyl-4-isothiazolin-3-one and 4,5-dichloro-2-n-octyl-4-isothiazolin-3-one.

3. The stabilized isothiazolone solution according to claim 1, wherein said solution comprises a stabilizer or stabilizers selected from the group consisting of N,N'-dimethyl-3,3'-dithiodipropionamide, N,N'-dimethyl-3-thiodipropionamide, methyl-3-mercaptopropionamide, 3,3-dithiodimethyl dipropionate, 3-thiodimethyl dipropionate, and methyl disulfide.

4. The stabilized isothiazolone solution according to claim 1, wherein said solution comprises a mixture of 5-chloro-2-methyl-4-isothiazolin-3-one and 2-methyl-4-isothiazolin-3-one.

5. The stabilized isothiazolone solution according to claim 1, wherein said isothiazolone solution comprises 2-n-octyl-4-isothiazolin-3-one.

6. The stabilized isothiazolone solution according to claim 1, wherein said solution comprises 0.1~20 wt % of isothiazolone expressed by said formula (I), 0.1~10 wt % of stabilizer expressed by said formula (II), and 70~99.8 wt % of organic solvent.

7. The stabilized isothiazolone solution according to claim 6, wherein said solution comprises 1~15 wt % of isothiazolone compound expressed by said formula (I), 1~5 wt % of stabilizer expressed by said formula (II), and 80~98 wt % of organic solvent.

8. A method of stabilizing isothiazolone, wherein an effective amount of stabilizer expressed by the following formula (II) is blended with isothiazolone expressed by the following formula (I):

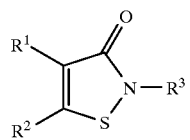

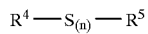

wherein, n, $R^1$, $R^2$, $R^3$, $R^4$, and $R^5$ have the same definitions as defined in claim 1.

* * * * *